United States Patent

Pedersen et al.

[11] Patent Number: 5,811,699
[45] Date of Patent: Sep. 22, 1998

[54] METHOD AND A SYSTEM FOR HANDLING SAMPLE MATERIALS, E.G. IN MIXING PLANTS, FOR CENTRAL ANALYSIS OF THE SAMPLES

[75] Inventors: Joan Grönkär Pedersen, Sjölund; Henning Jôrgensen, Kolding; Erik Huus Johnsen, Vejle; Ejner Paaske Jensen, Vorbasse, all of Denmark

[73] Assignee: Sprout-Matador A/S, Esbjerg, Denmark

[21] Appl. No.: 925,384

[22] Filed: Sep. 8, 1997

Related U.S. Application Data

[63] Continuation of Ser. No. 772,253, Dec. 23, 1996, abandoned, which is a continuation of Ser. No. 279,118, Jul. 22, 1994, abandoned, which is a continuation of Ser. No. 141,028, Oct. 25, 1993, abandoned, which is a continuation of Ser. No. 906,709, Jun. 30, 1992, abandoned, which is a continuation of Ser. No. 601,710, Jan. 7, 1991, abandoned.

[51] Int. Cl.[6] .................................................. G01N 1/00
[52] U.S. Cl. .................................... 73/864.81; 73/863.33; 73/863.83
[58] Field of Search ........................... 73/863.31, 863.33, 73/863.81, 863.83, 864.34, 864.81, 864.8, 864.83; 250/341, 358.1; 356/425

[56] References Cited

U.S. PATENT DOCUMENTS

| 3,673,700 | 7/1972 | Schabbel . |
| 3,827,302 | 8/1974 | Sato ...................................... 73/863.33 |
| 4,215,579 | 8/1980 | Hines et al. . |
| 4,236,404 | 12/1980 | Ketchum et al. ...................... 73/19.11 |
| 4,422,760 | 12/1983 | Webster . |
| 4,454,029 | 6/1984 | Codding .................................. 356/425 |
| 4,466,076 | 8/1984 | Rosenthal . |
| 4,694,165 | 9/1987 | Proctor et al. . |
| 4,849,625 | 7/1989 | Camerini Porzi . |

*Primary Examiner*—Robert Raevis
*Attorney, Agent, or Firm*—Antonelli, Terry, Stout & Kraus, LLP

[57] ABSTRACT

A method and system for handling simple materials in, for example, mixing plants, for enabling a central analysis of the samples. The samples are automatically and frequently taken from outlets of silos and are brought unwrapped and successively to an automatic near infrared reflection analyzing station through an pneumatic conveyor system with substantially common type sections between the station and the single samples. Sample portions which are larger than required for analysis are removed so as to counteract the risk of contamination of the samples, with the large sample portions then being returned to the silos of origin through another pneumatic conveyor system.

16 Claims, 3 Drawing Sheets

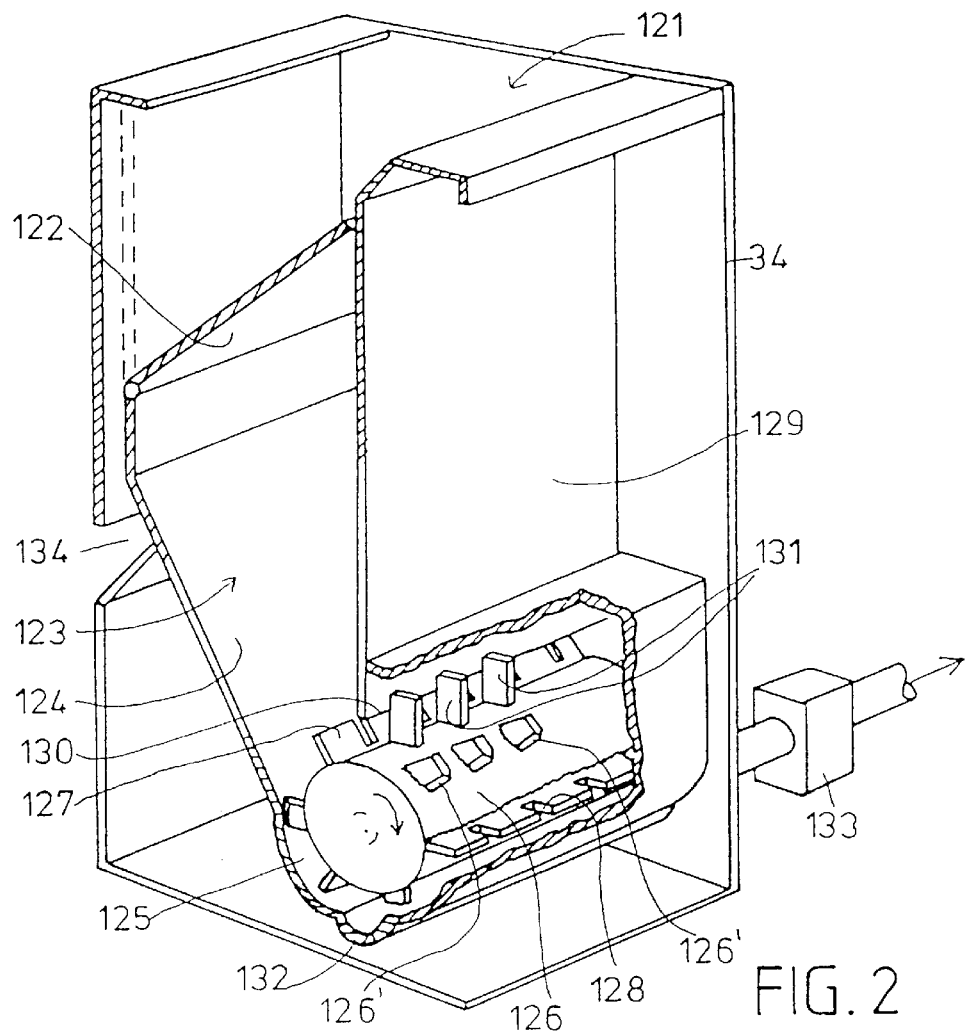
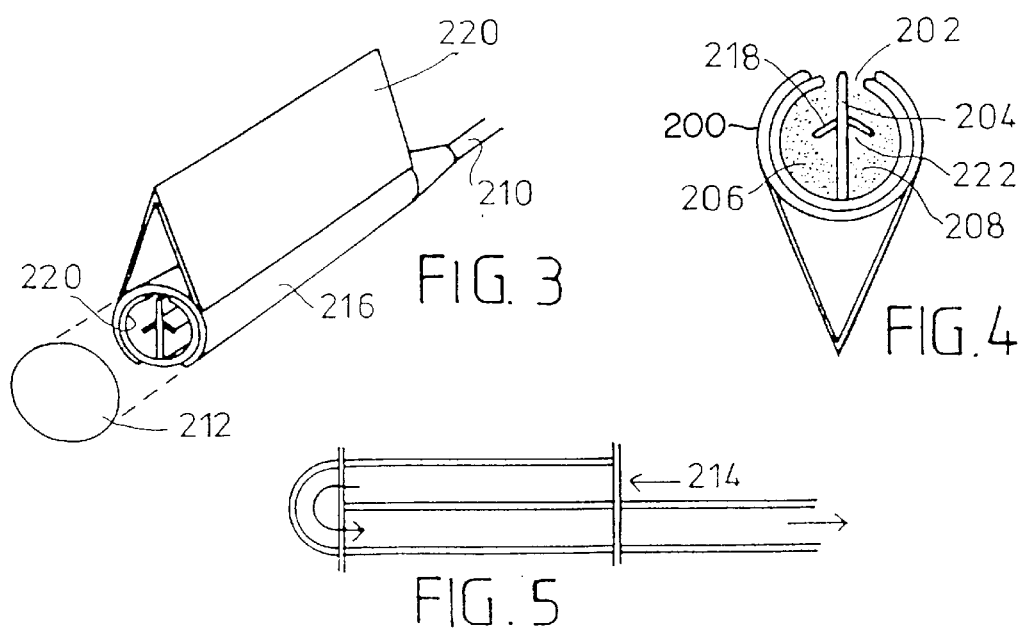

METHOD AND A SYSTEM FOR HANDLING SAMPLE MATERIALS, E.G. IN MIXING PLANTS, FOR CENTRAL ANALYSIS OF THE SAMPLES

This application is a continuation application of Ser. No. 08/772,253, filed Dec. 23, 1996, now abandoned, which in turn is a continuation application of Ser. No. 08/279,118 filed Jul. 22, 1994, now abandoned, which in turn is a continuation of application Ser. No. 08/141,028 filed Oct. 25, 1993, now abandoned, which is turn is a continuation of application Ser. No. 07/906,709 filed Jun. 30, 1992, now abandoned, which in turn is a continuation of application Ser. No. 07/601,710 filed Jan. 7, 1991, now abandoned.

FIELD OF THE INVENTION

The present invention relates to a method of handling sample materials in silo plants, mixing stations, process plants or generally in systems for reception, utilization or delivery of materials, in which material samples are frequently taken out at more places for being analysed in a central analyzing station, primarily though not exclusively in connection with the handling of animal or human foodstuff materials.

BACKGROUND OF THE INVENTION

In the production of fodder or foodstuff in industrial plants having, for example, a large silo battery for different material components, it is highly important that samples of the material components delivered from the single silos be taken out continually or at least as frequently as possible, such that corrections in the dosage or the material choice can be effected as early as possible in case of substantial changes of the contents of characteristic sub-components in the materials, for example, the contents of fat or protein in one or more of the raw materials. Quite elementary this may be effected by taking out from the outlet of a selected silo a material sample, which is carried to a central laboratory, from which the result of an analysis can be communicated after a certain lapse of time, all according to the capacity of the analyzing equipment, whereafter possibly desired corrections can be determined. During the recent years automatic analysis systems have been developed, which, based on very small samples, can accomplish a relevant analysis in only a few seconds, and it would be an opposite extreme, therefore, that such an automatic analyzing system could be mounted in connection with each single of the silo outlets for delivery of a continuous flow of analysis results for each particular material. It will be understood, however, that such an arrangement would be unrealistically expensive.

Also in various other materials handling and processing plants it would be important to obtain rapid analysis results from several sampling places, for example, for quality based account settling for received materials or for process controlling or goods declaration of delivered materials.

It would be an attractive arrangement to place a fast working analysis system in a central analyzing station and to deliver to this station material samples from the different sampling places rapidly after each other, but in large systems this will require a very complicated transportation arrangement, which, to date, has not been realized in practice. It has been proposed to fill the samples into tube cartridges which can then be conveyed to the central analyzing station through a pneumatic tube conveyor system, but this is considered unrealistic for several reasons. The conveying itself may be effected reasonably rationally, but severe problems will be connected with the handling of the materials by both the filling and the emptying of the cartridges, and sample contamination problems will occur at the delivery of the samples to the analyzer unit, where the sample may be contaminated by residue of the previous sample. Corresponding contamination problems will occur in systems where it is required to grind at least some of the involved material components prior to the analysis. An efficient grinding requires relatively expensive equipment, and, if separate grinding units of the single sampling places should be avoided, the samples should be delivered to a central grinding apparatus associated with the analyzer, whereby based on the prior art it will be almost impossible to avoid an essential contamination of the successive samples.

SUMMARY OF THE INVENTION

The present invention seeks to provide a method and a related handling system which will make it possible, in a realistic and advantageous manner, to work with local sample takings in connection with but a single or at most a few analyzers.

The invention is based on the consideration that it is reasonably simple to convey material samples all the way to the analyzer when this can be done through a pneumatic conveyor pipe with the sample in free and unwrapped condition, as it is hereby also possible, as in the pneumatic tube conveyor system mentioned above, to make use of certain common, partial conveying stretches of the system for finally transporting the samples to a single place of delivery. When it is possible and desired to make use of quite small sample portions, however, this manner of conveying the samples will be disqualified in advance, because the discussed sample contamination will be highly pronounced. In accordance with the invention, however, this inconvenience is counteracted by deliberately making use of relatively very large sample portions, e.g. several hundred times larger than the amount required for analysis itself, whereby possible remnants of previously conveyed sample portions present in the the common conveyor stretches will or can get mixed into the new sample portion in such a proportion which is low enough to be fully acceptable in view of the adequate analysing accuracy. Thus, no unrealistic attempt of cleaning the conveying path is done, in practice, the required portion sizes are reasonably moderate, for example, of the magnitude 1–6 liters, preferably 3–5 liters.

It is a strongly associated problem how a representative sample of a few grams can be derived from the relatively large sample portions. The relevant fast acting analyzers operate, based on the so-called NIR-principle (Near Infrared Reflection), where a sample of a thickness of few millimeters is subjected to a low frequency light. An isolation of a small sample may be obtained by repeated down-dividings of or from the large sample portion, but this is complicated, and problems as to correct representation of the down-divided sample are likely to occur in accordance with the present invention, the sample portions are successively collected in a correspondingly voluminous sample container in the analyzing station and the analysis is carried out based on surface irradiation such as NIR with the use of a detector head, which is brought to cooperate with surface area of the sample portion in the container, preferably, at a suitably prepared side wall area of the container. By virtue of these features of the present invention, it is possible to no longer utilize small sample portions, and as far as the entire large sample portion can be collected in a container, which, at a small surface area, may provide for operative access to carry out the discussed surface irradiation of the sample material. While it is sufficient that the irradiated material layer is a few millimeters thick it will be without influence on the analysis if the layer thickness is still much larger, so for this reason, the large sample portion may simply be collected in a simple, large container, in which any surface area of the material may be representative for the sample as a whole. Since considerable turbulences will occur in the pneumatic conveyor system the the remnants from previous sample transfers will not be liable to be present predominantly in the surface layer the material collected in the container, the remnants are more likely to be evenly distributed in the material of the new sample, and the analysis result, therefore, can be fully reliable within the applied tolerances.

The relatively large sample portions of for example 3–5 liters or maybe 2–10 liters will yet be comparatively quite small where the sample originates from a source of tons of material, but for one part the material component deliveries are often much smaller, and for another part a frequent sample taking is aimed at, whereby in both cases the relatively large test samples will represent considerable amounts of the respective materials. It is therefore advantageous and both operatively and construction-wise feasible to arrange for the sample portions, as far as possible, to be returned to the respective sampling areas, such that they are not wasted, for this purpose, sample portions, after being analyzed, may be conveyed, in accordance with the present invention, from the sample container through a selectively controllable pneumatic conveyor system back to the respective areas in which the samples originate.

It is considered essential that in the central analyzing station the single sample portions can be handled and thus also removed in a rapid manner, but it should be taken into account that an associated computer elaboration on the result of the analysis can take some time, even when short, and it can be very important to to hold back the sample until it has been ascertained whether the test result corresponds with an expectable result or whether it could be of special interest for a closer analysis for, for example, a recalibration or a reliability control of the entire analyzing system. If the sample gives rise to a deviation, yet expectable result, which is due to reasonably natural changes in the characteristics of the material, it can be relevant to arrange for a computer system to effect a correction of the dosing of the material, the choice of materials, or the accounting, but atypical changes may be due to a change of the analyzer calibration, and it may be desirable, therefore, to subject the actual sample to an accurate chemical analysis for providing further details to the computer. In such situations the entire sample portion could be isolated by a selective letting out from the NIR test container, but the relatively large sample portion would be quite unnecessarily large for a laboratory analysis, and besides it can be desirable, as mentioned, that the large portion or the main part thereof can be immediately returned to the place of origin. The samples after being analyzed, in accordance with the present invention, are released from the sample container through a sampling chamber in which a sampler, by an occurring atypical analysis is actuated for taking a modest subsample for a following closer analysis. The subsample preferably is fed to a packing unit for packing, identification marking and delivery of the thus packed sample. By virtue of the last mentioned features of the present invention it is achievable that a "sub sample" of a suitable small volume can be taken from the sample portion in the atypical situation, such that the test container will be made ready for receiving a next sample portion.

For the invention it is mandatory that the material in the samples, which, from the sampling areas, should be introduced into the pneumatic conveyor system, be comminuted sufficiently to be conveyable without forming accumulations in the conveyor system, and it is also a condition that the material is still finer comminuted by its introduction into the test container of the NIR analyzer, as a correct analysis is conditioned by an extensive comminution of the material. The comminution as required for the conveying can be effected locally by means of "coarse comminution" devices being arranged at all inlets to the conveyor system, while a further comminution as required for the analysis can suitably be effected in a central fine cutting device mounted immediately upstream of the analyzer.

Some sample portions may consist of a powder material that will need no further comminution before entry in the analyzer container or test chamber, but the provisionally "coarse comminuted" samples may be selectively guided through the said fine cutting device before that entry. Hereby it is advantageous that but a single, expensive fine cutting device will be sufficient, but it is an associated major problem that the fine cutting device must be able to handle the material in such a manner that there will not, in the device, be deposited substantial remnants of the treated material portions, as this would involve a considerable contamination of following samples. Already for this reason usual comminutors such as beater mills will be unusable, and instead there is provided a real fine cutting apparatus which can comminute the material finely by means of a rotating knife system such that 1) the comminution will be sufficiently fine for the purpose of the NIR-analysis, 2) practically no remnants from the successive sample portions will be left in the apparatus, and 3) the throughflow velocity of the successive samples will be controllable according to the requirements for subjecting the samples to individual degrees of working in order to obtain the required degree of comminution as fast as possible.

BRIEF DESCRIPTION OF THE DRAWINGS

In the following, the invention will be explained in more detail with reference to the drawing in which:

FIG. 2 is a sectional perspective view of a sample terminal,

FIGS. 3–5 are views illustrating a sample container

DETAILED DESCRIPTION

Figure 1:
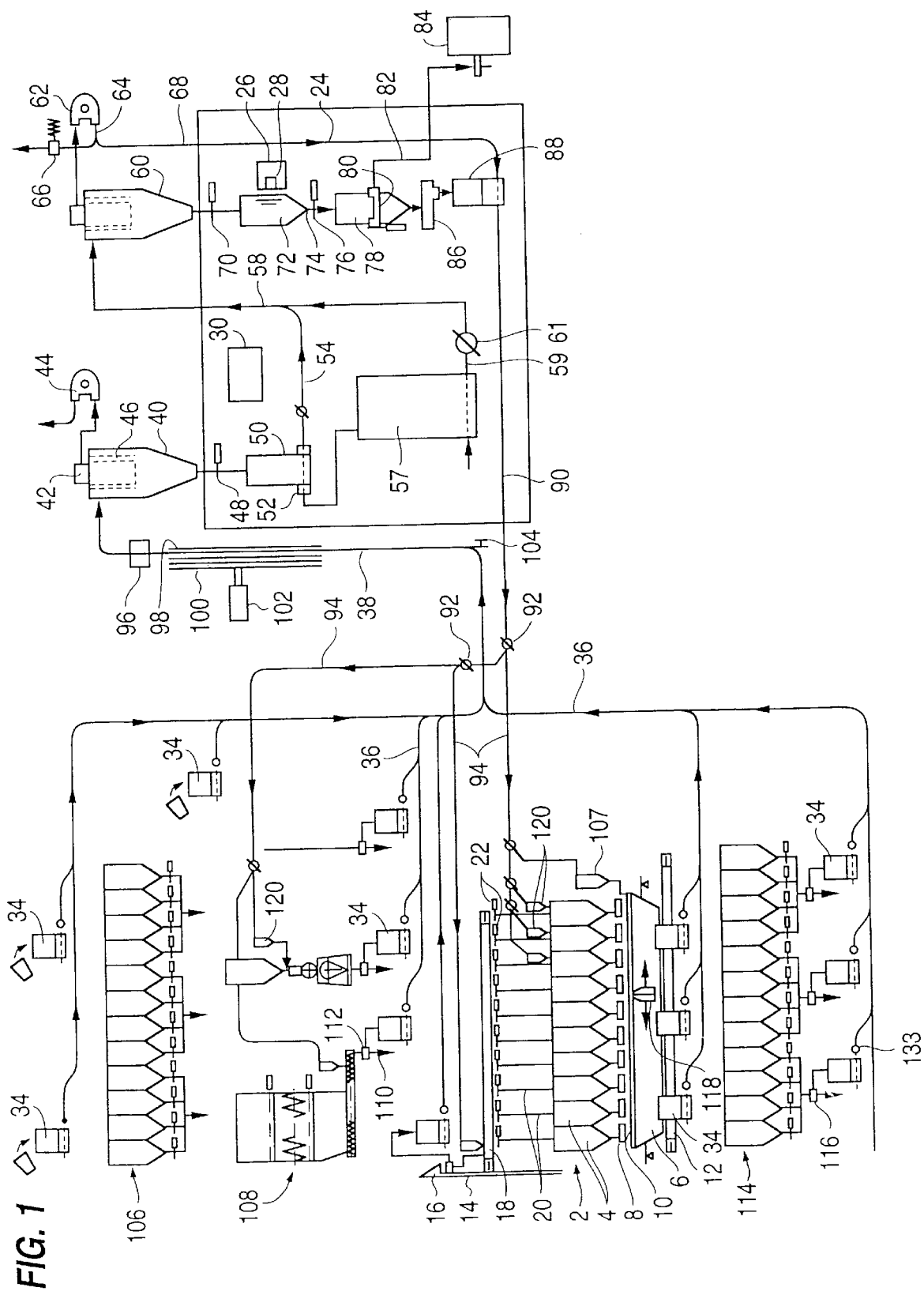
FIG. 1 is a schematic general plan of a system according to the invention.

In FIG. 1, a silo battery 2 includes single silos 4 arranged overhead the container of a so-called binweigher 6, and a controlled outlet means 8 is provided through which the materials from the various silos 4 can fall down into the container scales through respective outlets 10. The materials will be deposited on a lower conveyor 12 of the binweigher, and when the single portions have been successively dispensed, the conveyor 12 is actuated to deliver all the single portions to a non-illustrated mixer unit, which can then deliver the entire mixed portion to a lorry or tank truck or to a respective storage for that particular mixture. New raw materials may be supplied to the silos 4 from an elevator 14, at the top of which the material is fed through a downlet 16 to a conveyor 18 that moves the material over the tops of the silos 4 to a series of downlet connections 20, each having a closing valve 22, by means of which the downlet to just the relevant silo 4 can be opened.

The system so far described is a commonly known plant for the production of material mixtures, for example, mixed fodder, where different mixtures for different purposes can be prepared by selective actuation of the outlets 8,10. It is common practice to removed, from time to time, samples of the materials for closer analysis, viz. by the reception of the raw materials or where the materials are filled into the single silos. Hereby the raw material and the accounting for them can be checked and controlled all according to their contents of e.g. water and protein, and when changes occur it is possible to effect required adjustments of the mixing recipes for maintaining the essential constituents of the mixed products. However, the analyses are not too useful if their results are not at disposal before the single silo charges are used up.

Thus, it is far from being sufficient to removed samples of the raw material deliveries or of the material supplied to each silo 4, as it should rather be preferred to take out frequent samples at the outlets of the silos 4, but so far this has been considered practically impossible, because the silo outlets above the binweigher 6 are normally very difficult to approach.

By the invention it is endavored, however, to provide the possibility of a frequent, automatic sampling at these outlets and of a rapid conveying of the samples to a fast acting central analyzing station, which is connected with a computer equipment for rapid determination of recipe corrections, when required, and effectuation of these corrections, all in such a manner that registered quality changes in the raw materials can be compensated for already in the next following mixture portion or at least in the soon following mixture portions and possibly already in the same portion, by the preparation of which the change was registered. It is endavored to obtain an analysis approximately every minute and to keep the time lapse from a sampling to an effected recipe change derived therefrom so brief that it is of the same magnitude as the time for preparing a single average mixture portion, typically some six minutes. Inside this interval there may thus be effected more analyses of the various utilized raw materials.

All this is mainly achieved by five different measures, though with associated auxiliary measures, namely:

1) The sampling at the many silo outlets 10 is effected automatically with the use of a simplified sampling equipment which may consist of a single or just a few movable sampling devices;
2) The transfer of the samples to the central analyzing station is effected automatically through a pneumatic and fast acting conveyor system;
3) The samples are brought to the analyzing equipment or a few such equipments in a manner which is acceptable from an industrial point of view, that is with a substantially increased capacity compared with usual laboratory practice, and such that the successively handled samples will not leave remnants capable of contaminating the subsequent sample portion or portions as far as the analyses are concerned;
4) The samples are continually comminuted sufficiently to be automatically analyzable according to the NIR principle or corresponding principles; and
5) The analyser equipment is connected to an advanced computer system which can rapidly effect the required adjustments of the material dosings by occuring necessary recipe changes.

For carrying out these functions, the system according to the invention comprises an automatic sampling equipment, which is not disclosed in detail in the present disclosure, and an analyzing station 24 with an analyzer unit 26, which is preferably of the NIR-type, of conventional construction. The unit 26 has a detector head 28, which should be brought into close light radiation contact with the material samples, whereafter the unit 26 will rapidly produce an analysis result. This result can be read into a compute equipment 30, which will serve to effect the required adjustments of the mixing recipes in case the analyses reveal changes of the raw material qualities.

In the system shown use is made of a number of sample receiver terminals connected to a system of pneumatic pipe conveyors 36, which merge into a common suction pipe 38 connected with the suction inlet of a cyclone 40 arranged near the analysing station 24. The cyclone has an upper air outlet connected to a suction fan 44, and a cylindrical filter 46 is mounted about the associated central exhaust pipe from the cyclone. The material separated out in the cyclone leaves the latter through a valve 48 down to a collector container 50, at the bottom of which there is provided a transverse worm conveyor 52, which can be selectively actuated for discharging the material to either one or the opposite side. When discharged towards the right the material is taken to a conduit 54 connected with a suction pipe 58 leading to another cyclone 60, which is built just like the cyclone 40 and is connected with a separate suction fan 62. The air outlet therefrom is divided partly to the atmosphere through a valve 66 and partly to a return pressure conduit 68, the function of which will be explained below. Through a closing valve 70 the material outlet from the cyclone 60 is connected to a sample container 72, which is mounted in direct association with the NIR analyzing unit 26 and has a lower outlet pipe 74, which through a closing valve 76 leads to a flowthrough-container 78, in which there is mounted a sampler 80, from which a collected sample can be suctioned through a conduit 82 to a wrapping apparatus 84 for individual bagging of the samples. The main portion of the material will flow through the container 78 to a short worm conveyor 86, from which it is delivered to an outsluicing container 88, which at its bottom is connected with the pressure conduit 68 from the fan 62 and also with a continuing pneumatic conveyor pipe 90, which, through shift over valves 92, branches itself into a system of return carrying pneumatic conveyor pipes 94, through which the successively provided samples can be returned to the respective sampling areas.

As mentioned below the sample materials advanced through the pneumatic system to the analyzing station 24 will already be comminuted to such a degree that they can be conveyed in a safe manner, this being achievable by relatively cheap and coarse communition devices at each of the sample terminals 34. However, for a rapid and reliable NIR analysis it is essential that the sample material conveyed to the sample container 72 is really finely comminuted, and for achieving this there is mounted, in the analyzing station or in association therewith, a particular fine cutting apparatus 57, which can receive the material from the collector container 50 when the worm 52 is actuated to discharged the material towards the left. The finely cut material will leave the apparatus through a conduit 59, which is connected with the suction pipe 58 through a closing valve 61. A corresponding valve is mounted in the conduit portion 54.

In normal operation the successive portions of sample materials will be led through the fine-cutter 57 for delivery to the cyclone 60 and the sample container 72 in pronounced fine-cut condition, and a conveying through the conduit 54, which shunts the fine-cutter 57, is effected only in such cases, in which, for special reasons, it is directly undesirable that the material should pass the fine-cutter.

Another and more essential reason for letting the material bypass the fine-cutter 54 will be the finding of parts in the sample portion. The fine-cutter, which should be designed such that it can widely comminute the material without holding back small remnants of the material, will be a highly developed unit with a very fast rotating knife system that can treat the ordinary test materials highly effectively, but which will then also be quite vulnerable towards metal parts occuring in the material. Larger metal parts and other large foreign bodies in the material can be retained in grate structures in the sample terminals 34, but a required detection of smaller metal parts may be effected centrally, e.g. immediately by or prior to the letting in of the sample material into the collector container 50. In a simple manner this may be effected by a metal detector 96 mounted in connection with the suction conduit 38.

The collector container 50 should be able to collect a complete sample portion before this is conveyed further to the fine-cutter, viz. for ensuring that the entire portion can bypass the fine-cutter 57 whenever the metal detector 96 reveals the occurance of metal in any part of the incoming sample protion. A sample portion, thus contaminated, could well thereafter be directed directly to scrapping, as it will be unfit to be analyzed already due to the lacking fine-cutting thereof, but it has been found more practical just to let such sample portions be conveyed further through the described system, optionally for returning the sample portion to its sampling area or to the scrap silo, whereby care should be taken that neither the analyzer 26 nor the underlying sampler 80 be actuated by the occurance of samples of this type.

In FIG. 1 it is shown that along an upwardly conveying portion of the central suction pipe 38, which portion may consist of a pipe 98 of glass or another nonmagnetic material there may be mounted along this pipe an elongate magnet 100 that will act retaining on iron parts in the conveyed flow of material, such that at least a number of iron contaminated samples will reach to be cleaned sufficiently to thereafter be harmless to the fine-cutter 57 and not give rise to a distorted result of the analysis. The magnet can be mounted retractably from the pipe portion 98, by, for example, a cylinder 102, whereby the caught iron parts on the inner side of the pipe 98 may from time to time be released from the magnetic holding and thereby fall down through the pipe to a lower outlet valve 104.

To the system may belong a number of "loose" sample terminals 34, e.g. as shown at the top to the left in a laboratory or the like or in a store 106 for finished goods from which, on deliveries from the store, samples may be taken and manually poured into the sample terminal 34. These terminals have no fixed associated sampling areas, to which the samples can be returned after the analysis, and just these samples may then in stead be conveyed to a waste collecting area, for example, a so-called waste silo 107 in connection with the silo battery 2.

In FIG. 1 between the finished goods store 106 and the silo battery 2, it is shown that the plant may comprise various processing equipment 108 having outlets 110 provided with samplers 112, which deliver the samples to a sample terminal 34. As indicated, some units of this equipment may be suited to have the sample material returned from the pipe 90,94, while other of the units may not be so suited. At the bottom to the left is shown a finished goods store 114 with automatic samplers 116, which deliver the samples to respective sample terminals 34.

In connection with the binweigher 6, 12 is arranged a special sampling equipment comprising a sampler 118 which is movable along the row of outlets 10 from the silos 4, such that it is able to collect a sample from any of the outlets and bring the sample to one an more associated sample terminals 34. It is possible hereby to avoid using many separate samplers, and it will be possible to return the analyzed samples to the silos, from which they originate, or to the waste silo, through the illustrated feeding units 120.

For a safe transportation of the samples through the pneumatic system it is important that sample portions of coarse material are comminuted, and it is preferred, therefore, that those sample terminals 34, which are liable to receive coarse sample material, are provided as or with a comminuter device, and in practice it is preferred that all sample terminals be made in that manner. In connection with the invention a special comminuter or chopper has been developed which is additionally operative for a controlled sluicing in of the material to the lower sections of the sample terminals from which the material is suctioned into the conveyor system 36, 38, this terminal chopper being illustrated in FIG. 2.

The sample terminal 34 shown on FIG. 2 comprises a housing having an upper receiving opening 121 above a pivotal closing plate 122, which can be swung to an upright open position shown in dotted lines, so as to uncover a sample collector chamber 123 having an inclined bottom plate 124 leading to a lower half-cylindrical bottom portion 125. In this bottom portion is arranged a rotary cylinder 126 fitted with protruding knife members 126' and protruding, axially extending plate ribs 127 shaped with incisions 128. Above the middle of the rotor cylinder 126 a wall portion 129 has a lower extension 130 to which there is secured a series of upright flat iron pieces 131 projecting downwardly towards the cylinder 126 such that they can be passed by the incisions 128 in the plate ribs 127 and also be passed by the knife members 126' in the interspaces between the flat iron pieces 131.

Hereby the rotor cylinder 126 will act as both a chopper and sluicing-out member, which will bring the chopped material to the bottom portion 125. This portion has a lowermost gutter portion 132, which, at one end, is connected to the suction branch pipe 36 of the pneumatic conveyor system, while at the other end or side of the sample terminal it is open to the atmosphere. The pipe 36 is provided with a solenoid valve 133 controlled by the main control system.

When a sample is ready for delivery to the terminal, actuator means (not shown) are operated to open the top plate 122, and the entire sample is discharged into the collector chamber 123, whereafter the plate 122 is closed. When thereafter the control system asks for the particular sample to be supplied to the conveyor system the valve 133 is opened and the rotor 126 is started, whereby the sample material is chopped down into the gutter and successively drawn into the pipe 36 by the air flow along the gutter. Matter falling onto the closed top plate will be diverted down and out through a slot 134 in a wall portion of the terminal.

Thus, the relatively large sample portions are here supplied to the conveyor system in a gradual manner, so as to be continually moved away, each, by the air already flowing through the gutter. This, however, requires some sort of active sluicing into the air flow, because the pneumatic conveying cannot be initiated if the air passage is fully blocked by material to be conveyed. In some sample containers it may be unnecessary to make use of a chopper, and it could be desirable, then, to entirely avoid the motor driven system. This will also and particularly apply to such cases where it could be desirable to combine a sampler directly with a sample container, for example, a sampler to be moved across a flow a material and having its container portion connected with the conveyor system through a flexible hose. In many instances it will be preferred to actuate the sampler at a given time, when there is a flow to sample, and to defer the delivery of the sample to the conveyor system until it is relevant to carry out the analysis, so both here and in stationary sample receivers it could be desirable to start the suction from an already filled sample container.

FIGS. 3–5 exemplify a sampler designed for this purpose. It consists of a tubular body 200 having an axial top slot 202 and an upright middle partition 204 dividing the inner space in two halves 206 and 208. At one end the space 208 is connected with a hose 210 leading to the conveyor system through a solenoid valve (not shown), while at the other end the two halves are interconnected by a half-ball end cover 212. At the opposite end of the half 206 is an air intake opening 214. About the tube 200 is arranged a partially cylindrical cover 216, which is turnable between a closed and an open position relative the top slot 202. On the partition 204 is mounted a pair of opposed plate wings 218 projecting outwardly and downwardly over a partial width of the tube 200. On the cover 216, opposite the open slot thereof, may be arranged a protruding triangular deflector member 220.

When this sampler is placed in or moved through a falling flow of material to be sampled the tube body 200 may be filled up with material as illustrated in FIG. 4. However, due to the wings 218 there will be left respective air channels 222 underneath these wings which cannot be intruded by the falling material. These channels, at both sides of the partition 204, will amount to an unbroken air passage between the suction hose 210 and the air intake opening 214, and when suction is applied to the hose 210 it is thus possible to establish an air flow through the sample material and therewith to get the suctioning out of the material initiated and soon thereafter completed. This, of course, may require a closing of the slot 202 by means of the cover member 216.

It will be appreciated that the air channels 222 could also be produced underneath wings or other mainly horizontal shield means projecting inwardly from an outer side portion of the container 200 and that the container could of course be stationary as well.

The analyzer unit 26 may be adapted such that it is operable to effect the required adjustments inside certain limits for deviation of the material characteristics, while for quite atypical deviations it may be desirable to effect a closer and traditional chemical analysis which will also involve a check whether it could be the analysing unit which produces wrong results. The automatic control may hereby be so adapted that in case of an abnormally deviating analysis result the sampler 80 in the flow-through chamber 78 is actuated, such that a small amount of the relevant sample material can be isolated and brought to the wrapping unit 84 for collection in a bag, which may then be taken to a specialized analyzing laboratory. The wrapping or bagging unit 84 may be provided with computer controlled means for identification marking of the samples.

Figure 6:
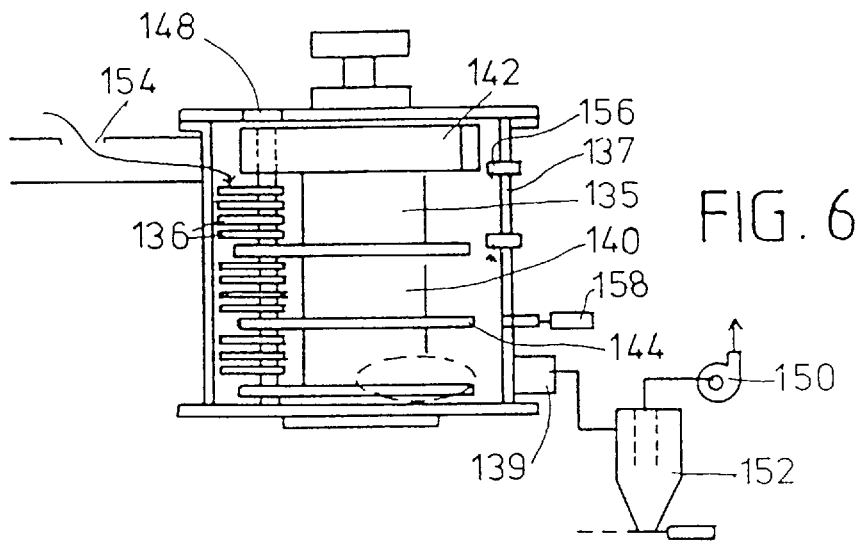
FIG. 6 is a sectional view of a sample comminutor.
Figure 7:
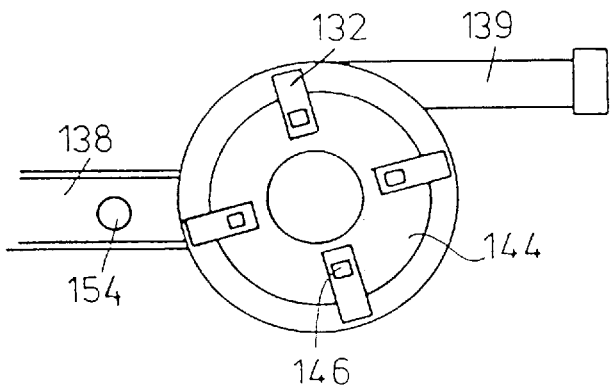
FIG. 7 is a sectional top view thereof.

FIGS. 6 and 7 illustrate a comminuter unit 57 particularly designed for the purpose of the invention. It is a cutter mill with a fast rotating knife rotor 135 having rigidly secured radial knives 136 rotating in a cylindrical housing 137, which has a lateral top inlet 138 and a tangential bottom outlet 139. The rotor is driven by a motor, not shown, and comprises a core 140 with a widened top portion 142 and with axially spaced plate flanges 144. At four places a rectangular steel rod 146 extends axially over the whole height of the rotor, through correspondingly rectangular holes in the members 142 and 144, and on these rods, in each space between the members 142 and 144, is mounted a series of interspaced knives 132 each having a rectangular hole for receiving the rod 146 in such a manner that the knives are mounted with a very high degree of rigidity on the rotor, this being unusual for an apparatus of this type. The purpose is to provide on apparatus of high efficiency with respect to capacity and cutting fineness, and, to this end, the rotor should operate very fast, e.g. 3000–6000 r.p.m., and the knife ends should sweep along the inside of the housing 137 at a very short distance therefrom, in practice some 1–1.5 mm. These conditions together impose upon the construction very high quality requirements for a safe operation, and hence the rigid mounting of the knives, and the mounting of the rotor in bearings at both ends.

The housing may have an openable side portion for inspection of the knives, and the rods 146 may be liftable through a hole 148 in the top cover of the housing when the knives are placed next to the opened side portion, such that knives may be changed without removing the rotor from the housing.

It is important to be able to control the material flow through the apparatus. This could be done by of compressed air nozzles mounted so as to blow the material downwardly, but a preferred arrangement is illustrated in FIG. 6, from which it appears that the cut material is suctioned out from the lower outlet 139 by a suction fan 150 and is separated by a cyclone 152, from which it is delivered to the analyzing station. The suction air is admitted to the housing 137 through the top inlet 138, in which there is provided a hole 154, and the air flow as shown by an arrow will then be generally downwardly directed inside the housing, whereby the material will be conveyed downwardly while being worked by the knives. By applying more or less suction to the outlet it is thus possible to control the flow-through time of the single sample portions for minimizing the time for producing a sufficiently finely cut material.

It is desirable to work with extremely sharp knives 136, what could necessitate a costly working of the knives. It has been found, however, that with the use of uniform knife members of case-hardened flat iron it is not necessary to carry out a sharpening of the knives, because after a relatively short commission period it will have happened that the edge of the intermediate layer of the knife members are noticeably worn, while the outer surface layers are practically not worn, such that very sharp edge protions will automatically be formed adjacent the upper and lower side of the projecting knife members.

As mentioned, air nozzles may be used inside the housing 134, but mainly for effecting a rapid blowing out of each treated material portion and for air rinsing of the interior thereafter. Such nozzles are shown at 156 in FIG. 6, arranged protruding into the housing, but, since the nozzles may then collect material on their top sides, they are preferably, as shown for the lower nozzle, arranged so as to be retractable by means of e.g. a cylinder 158 and to remain retracted during the periods of operation.

Figure 8:
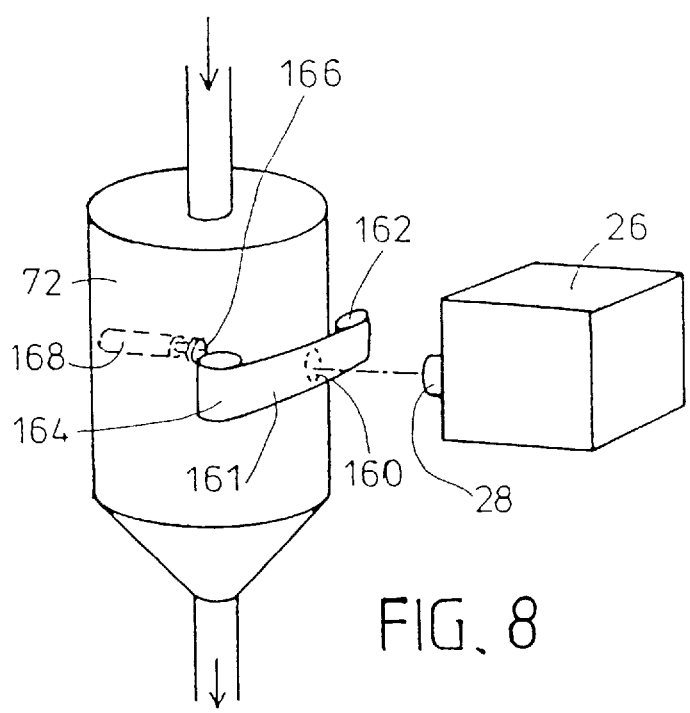
FIG. 8 is a perspective view of an associated NIR analyzing equipment.

It has already been mentioned that with the invention there will be another special problem, viz. the cleaning of the area outside the detector head 28, and one of the solutions to this problem is shown in FIG. 8, where the side hole in the sample container 72 is designated 160. The analyzing unit 26 is shown retracted from this hole, but normally the units may in fact remain closely juxtaposed. There is placed over the outer mode of the hole 160 a rolling film 161 consisting of a suitable transparent material such as Teflon, which has no substantial influence on the measuring result. This film is automatically drawn stepwise past the hole 160, from a supply reel 162 to a take up reel 164. Inside the container 72 is mounted a piston 166, which can be displaced crosswise by means of a pressure cylinder 168 so as to press the loose material in the container towards the hole 160 for enabling a correct analysis. The pressure will be taken up by the cover disc of the detector head 28, but with intermediary of the film 161, which will thus physically isolate the material from the cover disc.

After the analysis and the associated retraction of the piston 166 and removal of the material from the container 72, the film 161 is advanced a step for removal of the previous hole covering area and for covering the hole with a new and totally clean film piece, such that the next sample can be analyzed without any trace of the previous sample material being present. It will be understood that the film tape 161 could be replaced by a rotary disc, which may feed new and possibly successively cleaned film areas to the area outside the hole 160, as the hole covering parts of such a disc may be moved through an external station, in which means are provided for automatic cleaning of the disc material.

The film 161 and the reels 162 and 164 thereof may suitably be mounted in a cassette for easy replacement when the film is used up.

We claim:

1. A method of handling and analyzing samples of material in plants receiving, processing or delivering the material, wherein said samples of material may be contaminating, one to another, with respect to analysis of the respective samples of material, the method comprising the steps of:
   successively taking the samples from material stores at different places of the plant,
   transferring the respective samples directly to a pneumatic conveyor system having conveyor pipe lengths of which some are common to at least several of the material stores for the pneumatic transfer of samples therefrom such that remnants of previously conveyed samples in said common conveyor pipe lengths in the conveyor system, when mixed into a following sample, may contaminate the latter,
   successively successively conveying the respective samples in an unpacked condition to an analyzing station through said pneumatic conveyor system, and
   successively analyzing the respective samples of material to determine the content of a physical substance in the material of the sample by conducting an analysis of only a relatively small portion of the material of the sample, and
   wherein the respective samples which are taken, transferred and conveyed to said analyzing station have a sufficient volume, which is relatively large as compared with said relatively small portion, such that remnants of previous samples conveyed through said pneumatic conveyor system, when mixed with a following sample will contaminate the following sample, but only to an acceptable degree whereby an accurate analysis of the sample by the analyzing station can be attained through the analysis of said relatively small portion thereof without necessitating cleaning of said pneumatic conveyor system between conveyance of successive samples.

2. A method according to claim 1, wherein the samples are successively collected in a sample container in the analyzing station, and wherein the analysis is carried out by surface irradiation employing a detector head cooperable with a surface area of the sample portion in the sample container.

3. A method according to claim 2, further comprising the step of returning the respective samples after being analyzed from the sample container through a selectively controllable pneumatic conveyor system back to the respective areas from which the samples originated.

4. A method according to claim 2 further comprising the step of discharging the samples after the samples are analyzed from the sample container through a sampling chamber containing a sampler means for taking a subsample for enabling a subsequent further analysis, and feeding the subsample to a packing means for packing, identification marking and delivery.

5. A method according to claim 2, wherein the detector head is arranged at a side wall area of the sample container.

6. A method according to claim 1, wherein the step of taking samples includes feeding the respective samples to a sampler and from the sampler to the pneumatic conveyor system through an associated comminuter means for comminuting the material sufficiently to permit a pneumatic conveyance thereof, and wherein, prior to the conveyance of the sample to the analyzing station, the sample is fed through a fine-comminuter means for further comminuting the sample and conditioning the sample for the analysis by the analyzing station.

7. A method according to claim 1, wherein said samples are solid material in particulate form.

8. A method according to claim 1, wherein the volume of the sample is in a range of 1–8 liters.

9. A mixing or processing system for handling and analyzing samples of material respectively accommodated in a plurality of material stores, which samples may be contaminating, one to another, with respect to analysis of the respective samples of material, the system comprising means for controlling an amount of materials discharged from the respective material stores, sampling means for removing samples from outlet flow means of the respective material stores, means for analyzing the respective samples to determine the content of a physical substance in the material of the sample, said analysis being conducted on only a relatively small portion of the material of the sample, a branched pneumatic conveyor means for successively conveying the respective samples to a central analyzing station accommodating said means for analyzing, said pneumatic conveyor means having conveyor pipe lengths of which some are common to at least several of the material stores for the transfer of samples therefrom such that remnants of previously conveyed samples in said common conveyor pipe lengths in the pneumatic conveyor system, when mixed into a following sample, may contaminate the latter, wherein the sampling means are arranged so as to successively deliver the samples in an unpacked condition to respective inlets of the branched pneumatic conveyor means and wherein said means for controlling and said sampling means discharge and deliver sample portions of a volume, which is relatively large as compared with said relatively small portion analyzed by said means for analyzing, such that the sample volume being conveyed to said means for analyzing by said pneumatic conveyor means is very large relative to the volume of remnants from previously conveyed samples in said common conveyor pipe lengths in the pneumatic conveyor system, whereby said remnants, when mixed with a subsequent sample, will contaminate the subsequent sample, but only to an acceptable degree and an accurate analysis of the sample in the central analyzing station can be attained through the analysis of said relatively small portion thereof without necessitating cleaning of said pneumatic conveyor system between conveyance of successive samples.

10. A system according to claim 9, wherein the analyzing station comprises a sample container means for successively receiving at least a substantial part of the conveyed respective samples, and wherein said analyzing means irradiates a restricted surface area of the sample being analyzed portion.

11. A system according to claim 9, wherein an outlet end of the sample container is connected with a return conveying conveyor system through which the successive samples are returned to their respective places of origin.

12. A system according to claim 10, wherein said restricted surface area is defined by a window provided in a side wall of the sample container.

13. A system according to claim 9, further comprising material comminuting means disposed in connections between the sampling means and respective inlets of the pneumatic conveyor means for comminuting the samples sufficiently to enable conveyance in the pneumatic conveyor means.

14. A system according to claim 9, further comprising a central comminuter means for comminuting material of successively received samples preparatory to an analysis thereof, said central comminuter means being arranged in a connection between an outlet end of the pneumatic conveyor means and the central analyzing station, wherein said central comminuter means includes a cutter comprising a fast rotating knife rotor with fixed knives rotating in a housing very close to an inside thereof.

15. A system according to claim 9, wherein volume of the sample is in a range of 3–8 liters.

16. A system according to claim 9, wherein said samples are solid material in particulate form.

* * * * *